(12) United States Patent
Karmali

(10) Patent No.: US 8,148,339 B2
(45) Date of Patent: Apr. 3, 2012

(54) METHOD OF REDUCING CARDIAC LEVELS OF DOXORUBICIN WHEN GIVEN AS OROTATE SALT

(75) Inventor: Rashida A. Karmali, Brooklyn, NY (US)

(73) Assignee: Savvipharm Inc, New York, NY (US)

( * ) Notice: Subject to any disclaimer, the term of this patent is extended or adjusted under 35 U.S.C. 154(b) by 0 days.

(21) Appl. No.: 12/316,548

(22) Filed: Dec. 12, 2008

(65) Prior Publication Data

US 2009/0131344 A1     May 21, 2009

Related U.S. Application Data

(62) Division of application No. 11/496,255, filed on Jul. 31, 2006, now Pat. No. 7,470,672.

(51) Int. Cl.
*A61K 31/704*     (2006.01)
(52) U.S. Cl. ............................................ 514/34
(58) Field of Classification Search .................. None
See application file for complete search history.

(56) References Cited

U.S. PATENT DOCUMENTS

| | | | |
|---|---|---|---|
| 5,304,687 | A | 4/1994 | Bargiotti et al. |
| 5,605,703 | A | 2/1997 | Lambiez et al. |
| 6,210,930 | B1 | 4/2001 | Filippini et al. |
| 6,284,737 | B1 | 9/2001 | Farquhar et al. |
| 6,653,455 | B1 | 11/2003 | Johdo et al. |

OTHER PUBLICATIONS

Rosenfeldt F.I., Cardiovascular Drugs and Therapy 1998; 12: 147-152.
Theodoulou M, Hudis C., Cancer 2004; 100: 2052-6.

*Primary Examiner* — Timothy Thomas
(74) *Attorney, Agent, or Firm* — Rashida A. Karmali

(57) ABSTRACT

This invention is in the field of chemical restructuring of pharmaceutical agents known to cause tissue toxicity as a side effect, by producing their orotate salts. More particularly, it concerns orotate salts of the anthracyclines, doxorubicin and daunorubicin, that are found to reduce levels of the pharmaceutical agent in noncancerous tissues. The orotate salts are equally efficacious in inhibiting the SCCAKI-1 kidney tumor in animals and the reduction in the heart tissue of doxorubicin compared with doxorubicin HCl suggests a reduction in toxicity induced by free radical generation by the anthracyclines.

5 Claims, 6 Drawing Sheets

R = H; Daunorubicin
R = OH; Doxorubicin

Synthesis of doxorubicin orotate

METHOD OF REDUCING CARDIAC LEVELS OF DOXORUBICIN WHEN GIVEN AS OROTATE SALT

CROSS-REFERENCE TO OTHER APPLICATION

This application is a Divisional of U.S. patent application Ser. No. 11/496,255 filed on Jul. 31, 2006, and issued as U.S. Pat. No. 7,470,672 B2 issued on Dec. 30, 2008, which is incorporated herein, with references in its entirety.

FIELD OF INVENTION

This invention is related to orotic acid salts of pharmaceutical agents and in particular to the conversion of the cancer drugs to their orotate salts to reduce the tissue levels of the drugs in noncancerous tissues susceptible to drug toxicity.

1. BACKGROUND TO THE INVENTION

This invention is in the field of chemical restructuring of pharmaceutical agents known to cause toxicity or adverse drug reactions in noncancerous tissues as a side effect, by producing their orotate derivatives. More particularly, it concerns derivatives of the anthracyclines, doxorubicin and daunorubicin, that are used as anticancer drugs.

The antibiotic doxorubicin (DOX) and its salts, as well as other cationic anthracyclines currently are of great clinical interest in the treatment of cancer, including leukemias and solid tumors. Great hopes have centered on the use of liposomes as transport systems for bioactive agents. It has been established that the use of liposomes for the administration of anti-neoplastics in many cases improves the traditional methods of administration. Gabizon et al, Cancer Res. (1982), 42; 4234-4739 and Van Hossel et al, Cancer Res (1984) 44; 3698-3705. Different patents describe the inclusion of anti-free radical agents into liposomes having improved activity as inhibitors of lipid peroxidation. U.S. Pat. No. 5,605,703, issued Feb. 25, 1997. Liposomal encapsulation can substantially affect a drug's functional properties relative to those of the unencapsulated drug. In addition, different liposomal drug products may vary from one another in the chemical composition and physical form of liposomes. Such differences can substantially affect the functional properties of liposomal drug products. Doxyrubicin HCl which is the established name for (85, 105)-10-[(3-amino-2,3,6-trideoxy-(c-L-lyxo-hexopyranosyl) oxy]-8-glycolyl 1-7,8,9,10-tetrahydro-6,8,11-trihydroxy-1-methoxy-5,12-naphthacenedione hydrochloride. The molecular formula of the drug is $C_{27}H_{29}NO11HCl$; its molecular weight is 579.99.

DOXIL® (doxorubicin HCl injection) is doxorubicin hydrochloride (HCl), encapsulated in STEALTH® liposomes used for intravenous administration. The STEALTH® liposomes of DOXIL® are formulated with surface-bound methoxypolyethlyene glycol, a process often referred to as pegylation, to protect liposomes from detection by the mononuclear phagocyte system and to increase blood circulation time.

STEALTH® liposomes have a half-life of approximately 55 hours in humans. They are stable in blood, and direct measurement of liposomal doxorubicin shows that at least 90% of the drug remains liposome-encapsulated during circulation.

Experience with DOXIL® at high cumulative doses is limited and therefore it is assumed that DOXIL® will have myocardial toxicity similar to conventional formulations of doxorubicin HCl. Irreversible myocardial toxicity leading to congestive heart failure often unresponsive to cardiac support therapy may be encountered as the total dosage of doxorubicin HCl approaches 550 mg/m². Swelling, headache, chills, back pain, tightness in the chest or throat, and/or hypotension have occurred in up to 10% of patients treated with DOXIL®. In most patients these reactions resolve over the course of several hours to a day once the infusion is terminated. In some patients the reaction has resolved with slowing of the infusion rate. Serious and sometimes life-threatening or fatal allergic reactions have been reported.

Doxorubicin has been successfully administered by a wide range of schedules, and the anti-tumor activity of doxorubicin is proportional to the area under the concentration×time curve (AUC) not to peak drug levels. The AUC for concentrated doxorubicin HCl is 9.9 mg/ml-h. The AUC (mg/ml-h) for DOXIL® is 590.

Cardiac Toxicity—The cardiac toxicity exhibited by doxorubicin and the other anthracyclines is unique in terms of its pathology and mechanism. The major limiting facts in the clinical use ofanthracylclines in adults are bone marrow suppression, mucositis, and drug resistance on the part of the tumor. However, in individual patients, most commonly with the use of doxorubicin to treat breast cancer, cardiac toxicity can develop while the patient's tumor is still responsive to the drug. This is a problem not only for the use of the anthracyclines alone or in combination with other chemotherapeutic agents but also for the use of the monoclonal antibody trastuzumab and an antibody directed against HER2/neu oncoprotein, which is itself active in the treatment of advanced breast cancer. The observed potential of anthracycline-induced heart damage by trastuzumab has eliminated its use with doxorubicin in the population of patients whose tumors exhibit high levels of HER2/neu expression. Children seem to be more sensitive to the cardiac toxicity of this drug, and this has become a significant problem in the use of doxorubicin in pediatric oncology. Management of Drug Toxicity, Ch 31-42, in The Chemotherapy Source Book, $3^{rd}$ ed, Michael C. Perry, Lippincott Williams & Wilkins, 2001.

Thus there is a great need for analogues which give a better rate of response, a wider spectrum of response, and/or reduce cardiotoxicity. Halogenated anthracyclines, mechanistically different from doxorubicin and daunorubicin, have been produced. In particular, derivatives that have fluorine groups attached to their sugar moieties have a strong ability to kill tumor cells. Much of the history and prior art of doxorubicin is found in issued patents and published literature. See U.S. Pat. Nos. 5,304,687 issued Apr. 19, 1994; 5,605,703 issued Feb. 25, 1997; U.S. Pat. No. 6,210,930 issued Apr. 3, 2001; U.S. Pat. No. 6,284,737 issued Sep. 4, 2001; and U.S. Pat. No. 6,653,455 issued Nov. 25, 2003.

However, the present invention is distinguishable from the prior art because none of the prior art addresses the issue of preventing and/or reducing the levels of drugs in noncancerous tissues, as a strategy to reduce the toxicity and adverse drug reactions. More effective and less toxic agents are widely sought and are a fundamental object of the invention. The pertinent subject matter of the above references is specifically incorporated herein by reference.

3. SUMMARY OF THE INVENTION

The present invention seeks to overcome drawbacks inherent in the prior art by providing compositions of orotate derivatives of pharmaceutical agents that display increased clearance the pharmaceutical agents from noncancerous tissues that are targets for drug toxicity when compared with non-derivatized forms of pharmaceutical agent.

This invention is in the field of chemical restructuring of pharmaceutical agents known to cause tissue toxicity as a side effect, by producing their orotate derivatives. More particularly, it concerns orotate derivatives of the anthracyclines, doxorubicin and daunorubicin, that are used as anticancer drugs.

In view of the foregoing state of the art, the inventor has designed orotate derivatives of anthracyclines, as exemplified by doxorubicin orotate and daunorubicin orotate, containing therein a chemical organic moiety that reduces heart tissue levels of anthracyclines, of general formula A. FIG. 1.

A principle objective of the invention is to obtain a composition of doxorubicin or daunorubicin, their orotate derivatives and analogous compounds in order to reduce the toxicity of the drug, which is related to tissue levels of the drug accumulated in the heart.

The invention also specifically provides a process for the preparation of doxorubicin orotate and related derivatives starting from doxorubicin HCl, orotic acid and potassium hydroxide. This process comprises reacting potassium hydroxide with orotic acid, extracting the potassium orotate, and reacting the potassium orotate extracted with doxorubicin HCl to form doxorubicin orotate.

Another objective of the invention is to provide a method for treating human neoplasms, and particularly, primary or metastatic tumors, proliferative hematopoietic disorders and leukemias with doxorubicin orotate and reducing the toxic secondary effects of the drug by reducing the levels of the drug in noncancerous tissues that are susceptible targets of drug toxicity, by 10% to 100% when compared with giving doxorubicin HCl.

The invention provides methods of reducing levels of a pharmaceutical agent in noncancerous tissues, said methods comprising the steps of converting said pharmaceutical agent to an orotate derivative composition, administering said orotate derivative to a subject in need thereof, and measuring the levels of said pharmaceutical agents in noncancerous tissues, wherein said pharmaceutical agents are selected from the group of consisting of acetanilide, actinomycin D, adriamycin, aminoacridine, aminoimidazole, aminoquinoline, anilide, anthracycline antibiotic, antiestrogen, benzazepine, benzhydryl compound, benzodiazepine, benzofuran, cannabinoid, cephalosporine, cisplatin, colchicines, cyclic peptide, cyclophosphamide, daunorubicin, dibenzazepine, digitalis glycoside, dihydropyridine, doxorubicin, epiphodophyllotoxin, epirubicin, ergoline, ergot alkaloid, etoposide, 5-fluorouracil, idarubicin, ifosamide, imidazole, interleukin-2, interferon alpha isoquinoline, macrolide, melphalan, methotrexate, mitomycin-C, mitoxantrone, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyrimidine, pyrrolidine, pyrrolidinone, quinazoline, quinoline, quinine, rauwolfa alkaloid, retinoid, salicylate, steroid, stilbene, sulfone, sulfonylurea, tamoxifen, taxol, taxotere, THP-adriamycin, trastuzumab, triazole, tropane, vinblastine, vincristine or vinca alkaloid. alkaloid.

In some embodiments of the invention, the anthracyline orotate derivatives have the general formula:

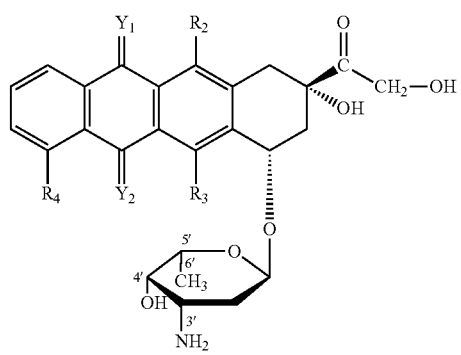

wherein:
R.$^1$ is a hydrogen (—H) group, a hydroxyl group (—OH), a methoxy group (—OCH.$_3$), an aryl group having 6-20 carbon atoms, a fatty acyl group having the general structure —O—CO(CH.$_2$)$_n$ CH$_3$, wherein n=an integer from 1 to about 20, or a fatty acyl group having the general structure —O—CO(CH.$_2$).$_1$ (CH.═CH).$_m$ (CH$_2$).$_n$ CH.$_3$, wherein l is an integer between 1 to 3, m is an integer between 1 and about 6, and n is an integer between 1 to about 9;

each of R.sup.2 and R.sup.3 is, independently of the other, a hydrogen (—H) group, a hydroxyl group (—OH), a methoxy group (—OCH.$_3$) or a double bonded oxygen moiety;

R.sup.4 is a hydrogen (—H) group, a hydroxyl group (—OH), a methoxy group (—OCH.$_3$), or a halide; and each of Y.$^1$ and Y.$^2$ is, independently of the other, a hydrogen (—H) group; a hydroxyl group (—OH); a methoxy group (—OCH$_3$); or a double bonded oxygen, sulphur, or nitrogen group.

4. BRIEF DESCRIPTION OF FIGURES

Figure 3:
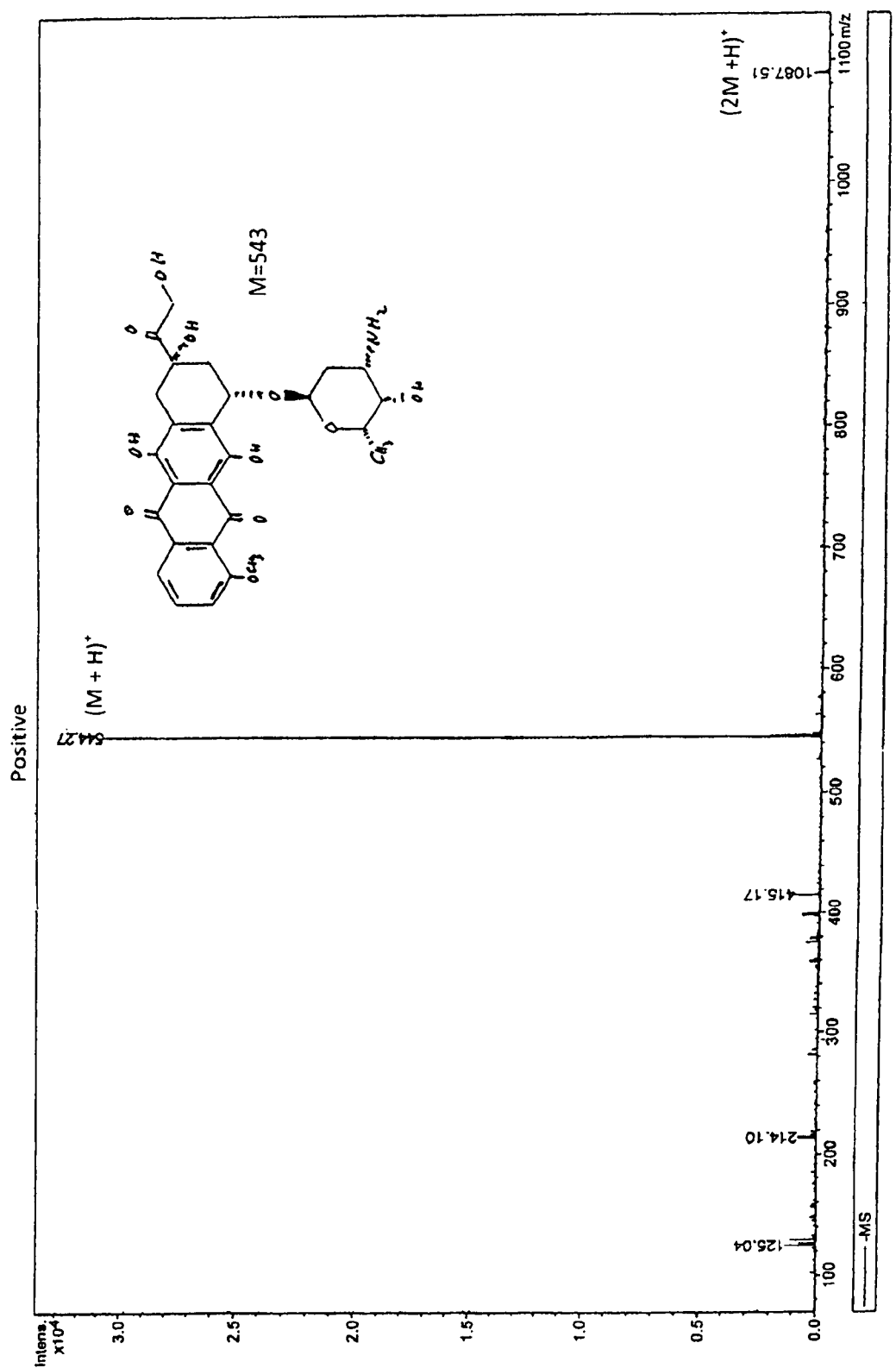

FIG. 3 Mass Spectrograph illustrating Doxorubicin orotate

Figure 4:
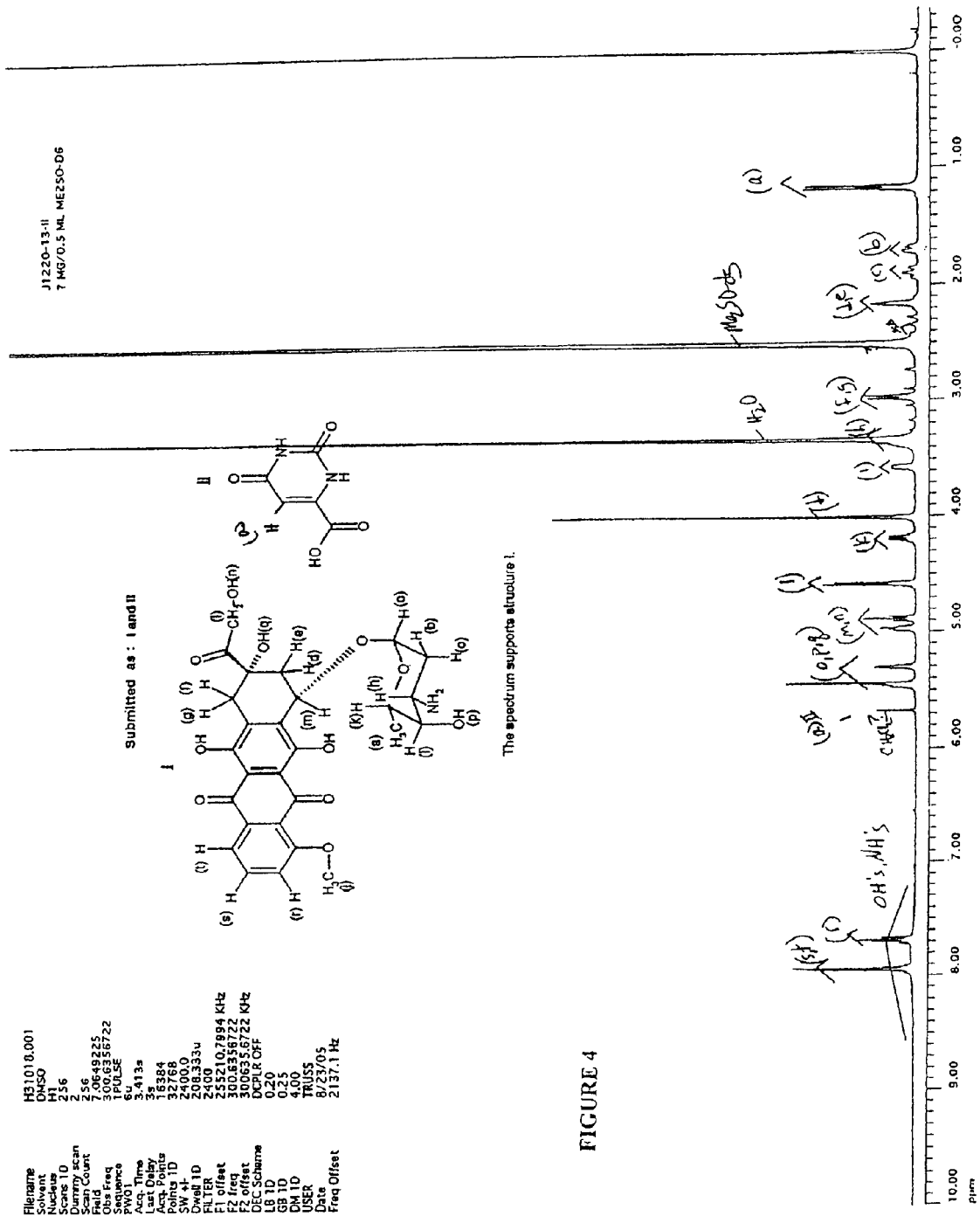

FIG. 4 NMR illustrating Doxorubicin Orotate

Figure 5:
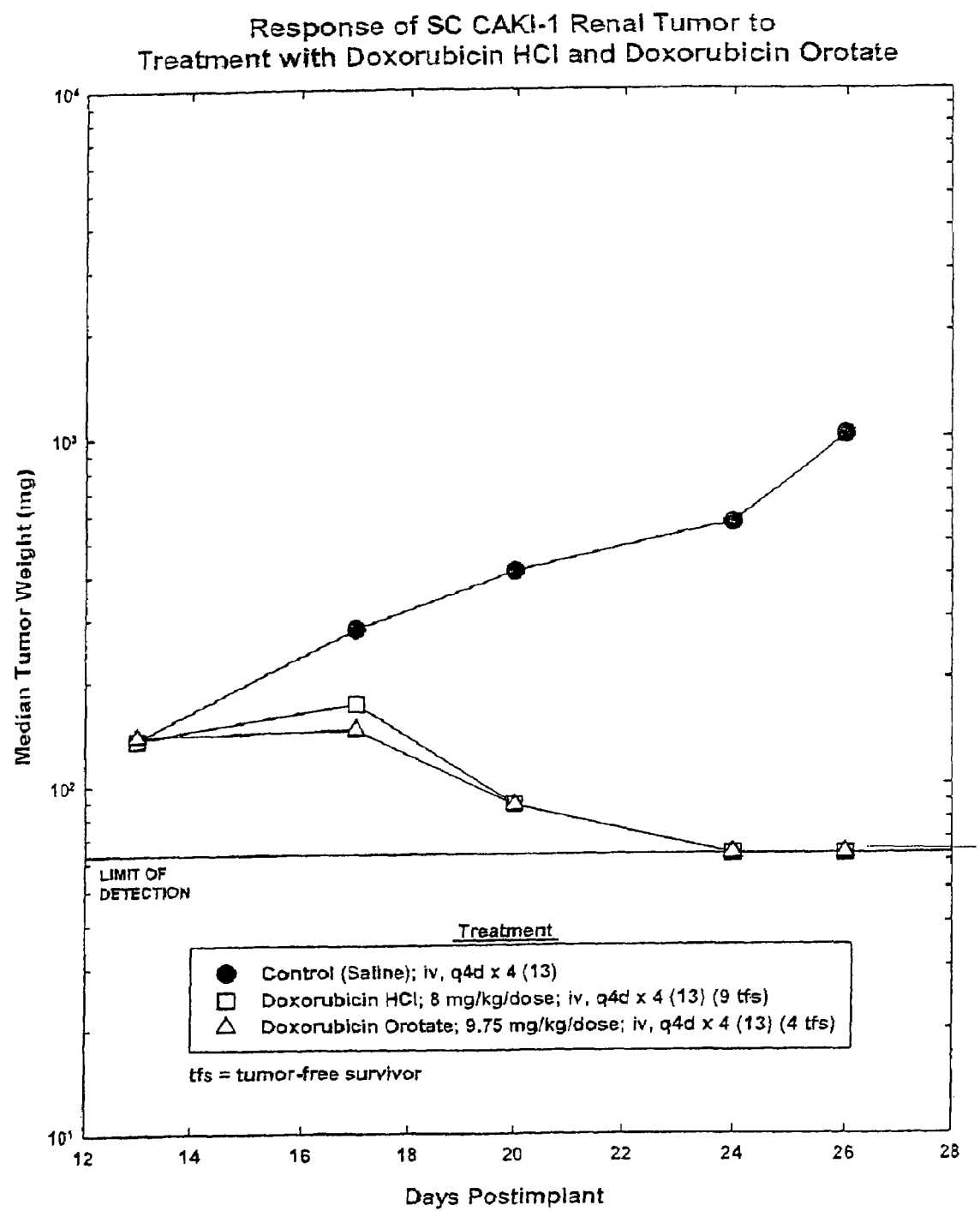
Figure 6:
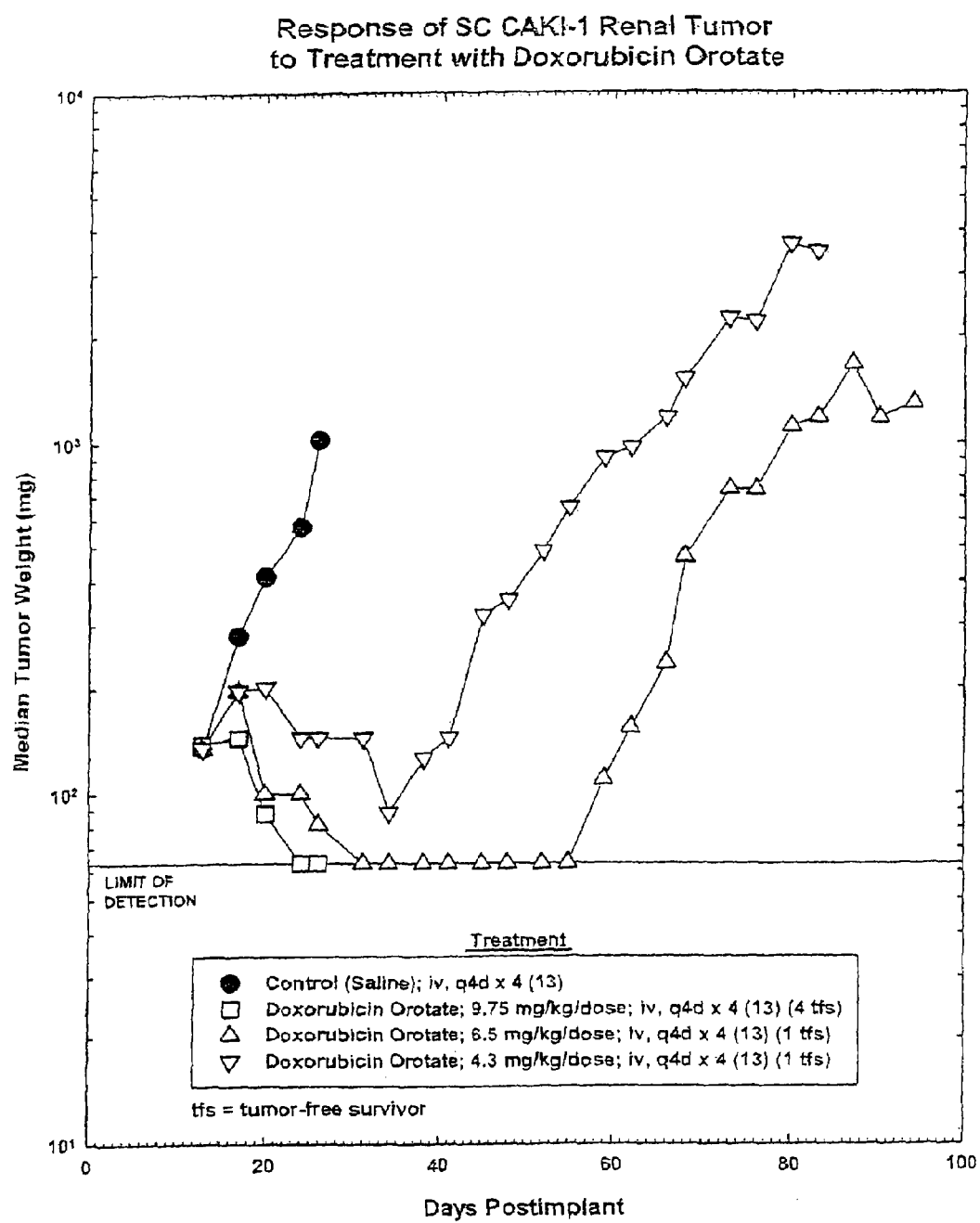
Figure 7:
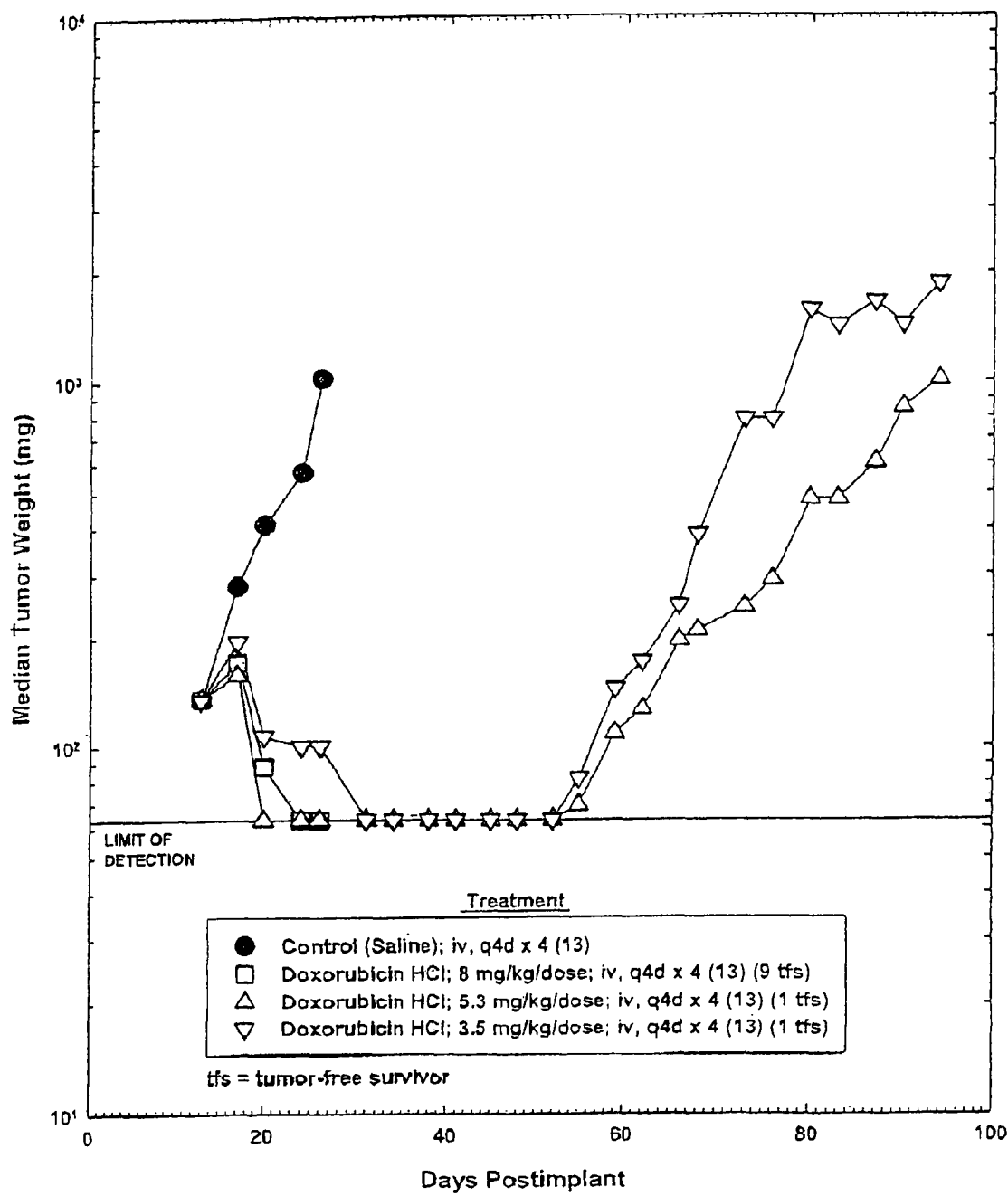

FIG. 5 illustrates the response of SC CAKI-1 Renal Tumor to treatment with Doxorubicin HCl FIG. 6 illustrates the response of SC CAKI-1 Renal Tumor to treatment with Doxorubicin Orotate FIG. 7 illustrates the response of SC CAKI-1 Renal Tumor to treatment with Doxorubicin HCl or Doxorubicin Orotate

5. DETAILED DESCRIPTION OF THE INVENTION

Drug therapies that art used for the treatment of patients with cancer can damage a number of organs and organ systems. Among those most frequently damaged are tissues with rapid cell turnover, such as the hematopoetic system, the gastrointestinal tract, and the genitourinary tract. The heart, made up of tissue without rapid cell turnover and therefore incapable of rapid recovery, is occasionally affected by chemotherapy. Because the cardiac effects of such therapy may be disabling or life threatening, it may necessitate a major modification of treatment to prevent cardiac toxicity. In some instances the effects of the chemotherapeutic drugs on the heart are self-limited and readily reversible with the withdrawal of the offending agent. However, in others the damage may be devastating, progressive, irreversible and ultimately fatal. Some forms of cardiotoxicity are poorly predictable and may affect patients without warning, sometimes during the first exposure. In other setting the toxicity is well defined and readily predictable. Yet there is considerable variation in the exposure needed to achieve similar levels of tissue damage.

Some drugs are toxic by themselves, but their toxicity may be potentiated when they are used in combination with other agents, the combination may be more toxic than the sum of the toxicities of the individual components. As it is necessary to achieve the greatest antitumor potential of the drug while keeping end-organ toxicity at an acceptable level, the evaluation of patients treated with toxic drugs must be individualized.

Most cardiotoxic drugs can be grouped according to their cardiac effect; for example 1) drugs associated with myocardial depression (e.g., anthracyclines—doxorubicin, THP-adriamycin, idarubicin, epirubicin, daunorubicin—; other anthraquinones—mitoxantrone, toxicity intensifiers such as cyclophosphamide, mitomycin-C, etoposide, melphalan, vincristine or bleomycin, and other agents—interferon alpha and trastuzumab); 2) anticancer agents associated with ischemia e.g., 5-fluorouracil, vinblastine, vincristine, cisplatin, or interleukin); 3) anticancer agents associated with hypotension (e.g., interleukin-2); and 4) miscellaneous agents with cardiac toxicity (e.g., paclitaxel, actinomycin D, mitomycin C or ifosamide).

Doxorubicin, the most widely used agent in the anthracyline group has been studied extensively and serves as a model for drug associated cardiac toxicity and myopathies. Its effectiveness is in part limited by the cumulative dose-related cardiotoxicity, which usually occurs late during a course of treatment or may present months or years after the completion of therapy. This suggests strongly that there may be drug residues left in the tissue after the therapy is completed. Therefore, there is a critical need to reduce and/or prevent the drug from accumulating immediately at termination of the therapy as well as subsequently in the short and long term in the noncancerous or non-diseased tissue.

In particular, the presentation of toxicity is slowly progressive, potentially irreversible, and life threatening. The pathogenesis of doxorubicin-associated cardiomyopathy has not been fully elucidated, and the exact mechanism of cardiotoxicity in patients who are treated with doxorubicin and related drugs, as well as the sequence of events that leads to cardiac dysfunction is still under investigation. However, there is no question that the accumulation of doxorubicin and related drugs in the cardiac tissue leads to progressive cardiac dysfunction and damage and therefore it is an objective of the present invention to reduce and/or prevent the accumulation of drugs and their metabolites in the target organ such as the heart. It appears that doxorubicin causes direct damage to membrane lipids as well as indirect damage through oxygen-free radicals that affect the calcium transport and eventually depress cardiac function. It is therefore vital that accumulation of doxorubicin in the heart tissue be reduced or prevented entirely to reduce the potential short-term and long-term side effects of the drug.

Doxorubicin cardiomyopathy may become manifest months and even years after successful completion of a course of chemotherapy at or near the maximum tolerated dose. As a greater number of patients treated with doxorubicin are cured and therefore survive for long periods of time after their chemotherapy, some patients who have significant but subclinical cardiac damage may experience additional stresses that may be poorly tolerated and result in symptomatic cardiac dysfunction months or years after the initial cardiac insult. It is an objective of the present invention to reduce the magnitude and occurrence of that initial cardiac insult caused by the drug, by reducing the levels of the drug in the heart by preventing accumulation and/or ensuring faster clearance of the drug from the cardiac tissue when chemotherapy is administered.

In animal models it has been observed that the encapsulation of doxorubicin in liposomes significantly reduces the secondary effects of toxicity, both chronic and acute. Rahman et al, Cancer Res (1980) 40; 1532-1537, Gabizon et al, J. Natt Cancer Inst (1986) 77; 459-467. Other indicators of toxicity, such as alopecia, loss of weight, nausea, vomiting, and dermal necrosis produced by extravasate may be reduced in significant manner by the administration of doxorubicin in liposomes. Forssen et al, Cancer Treat Rep (1983) 67; 481-484. Importantly, it has been established in various tumor models that this significant reduction of the toxicity is not produced at the expense of reduction of the antitumor efficacy.

The cardiomyopathy observed in treatments with doxorubicin is similar to the lesions seen in the cardiac muscles in experimental animals under conditions of alpha-tocopherol deficiency. These results suggest that the lesions produced by the drug are caused by an increase in free radical reactions in which lipids of membrane are seen to be involved. Therefore, the incorporation of doxorubicin, herein after DOX, into the lipid bilayers of the liposomes may facilitate the unleashing of free-radical type reactions. Accordingly, the levels of free radicals in DOX exposed noncancerous tissues are measured by biochemical methods to demonstrate that the orotate derivative of DOX reduces their levels.

It is an objective of the present invention to reduce the magnitude and occurrence of that initial cardiac insult caused by the drug, by reducing the levels of the drug in the heart by preventing accumulation and/or ensuring faster clearance of the drug from the cardiac tissue when chemotherapy is administered thereby reducing the release of free radicals.

Characteristics of Drugs Used as Orotate Derivatives

The word "drug" as used herein is defined as a chemical intended for use in the treatment or prevention of disease. Drugs include synthetic and naturally occurring bioaffecting substances as well as recognized pharmaceuticals, such as those listed in "The Physician desk Reference," 56th ed, pages 101-133 (or an updated edition). These references are incorporated by reference herein. The term "drug" also includes compounds that have the with drugs consisting of charged, uncharged, hydrophilic, zwitter-ionic, or hydrophobic species, as well as any combinations of these physical characteristics. A hydrophobic drug is defined as a drug which in its non-ionized form is more soluble in lipid or fat than in water. A preferred class of hydrophobic drugs is those drugs that are more soluble in octanol than in water.

Compounds or drugs from a number of classes of compounds can be converted to orotate derivatives and administered orally as orotate derivatives. The compound or drug can be for example, but is not limited to the following classes: acetanilide, actinomycin Dadriamycin, aminoacridine, aminoimidazole, aminoquinoline, anilide, anthracycline antibiotic, antiestrogen, benzazepine, benzhydryl compound, bezodiazpine, benzofuran, cannabinoid, cephalosporine, cisplatin, colchicines, cyclic peptide, cyclophosphamide, daunorubicin, dibenzazepine, digitalis glycoside, dihydropyridine, doxorubicin, epiphodophyllotoxin, epirubicin, ergoline, ergot alkaloid, etoposide, 5-fluorouracil, idarubicin, ifosamide, imidazole, interleukin-2, interferon alpha isoquinoline, macrolide, melphalan, methotrexate, mitomycin-C, mitoxantrone, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyrimidinc, pyrrolidine, pyrrolidinone, quinazoline, quinoline, quinine, rauwolfa alkaloid, retinoid, salicylate, steroid, stilbene, sulfone, sulfonylurea, tamoxifen, taxol, taxotere, THP-adriamycin, trastuzumab, triazole, tropane, vinblastine, vincristine or vinca alkaloid.

"Side effects" or "toxicity" or "adverse drug reactions" of chemotherapeutic agents are observed in the acute phase of chemotherapy administration and in patients cured of the cancer with subclinical tissue damage. There is a higher recognition of drug-related tissue side effects which may be quite severe, disabling and irreversible. The clinician must be aware of the potential tissue/organ complications of chemotherapeutic agents and where appropriate perform a baseline tissue examination before initiating the therapy.

"Clearance" of drug occurs by perfusion of blood to the organs of extraction. "Extraction" refers to the proportion of drug presented to the organ which is removed irreversibly (excreted) or altered to a different chemical form (metabolism). Clearance (CL) is therefore calculated as the product of the flow of blood through the organ and proportion of the drug extracted by the organ.

Clearance of drug normally occurs from the liver and kidneys and it is assumed that only free and not protein bound, drug is available for clearance. For hepatic clearance, passive diffusion through the lipid core of the hepatocyte membranes, available to lipophilic drugs, is augmented by sinusoidal carrier systems particularly for ionized molecules (anionic and cationic) of molecular weights of above 400. Likewise other transporters on the canalicular face transport drugs or their metabolites into bile. This system has two separate processes, hepatic uptake and biliary excretion. With small sized lipophilic drugs that readily traverse membranes hepatic uptake is not a major factor, but with higher molecular weight compounds (above 500) and those containing considerable H-bonding hepatic uptake can become the key clearance process, even if metabolism occurs subsequent to this.

The present invention provides a method to increase clearance of the orotate derivatives of the pharmaceutical agent from noncancerous tissues as measured by pharmacological studies at least 25% relative to dosing of the pharmaceutical agent. The invention also provides a method to increase clearance of the orotate derivatives of the pharmaceutical agent from noncancerous tissues as measured by pharmacokinetic studies of at least 50% relative to dosing of the pharmaceutical agent. The invention further provides a method to increase in clearance of the orotate derivative of the pharmaceutical agent from noncancerous tissues as measured by pharmacological studies of at least 100% relative to dosing of the pharmaceutical agent.

The present invention provides a composition that increases clearance of the orotate derivative of the pharmaceutical agent from noncancerous tissues as measured by pharmacological studies of at least 50% relative to dosing of the pharmaceutical agent. It also provides a composition that increases in clearance of the orotate salt of the pharmaceutical agent from noncancerous tissues as measured by pharmacokinetic studies of at least 100% relative to dosing of the pharmaceutical agent. It further provides said composition that increases in clearance of the orotate derivative of the pharmaceutical agent from noncancerous as measured by pharmacokinetic studies of at least 100% relative to dosing of the pharmaceutical agent.

Absorption or efflux occurs by one of three methods, either passive diffusion, active transport or facilitated active transport. Passive diffusion is simply the passage of molecules across the mucosal barrier until the concentration of molecules reaches osmotic balance on both sides of the membrane. In active transport the molecule is actively pumped across the mucosa. In facilitated transport, a carrier generally a protein, is required to convey the molecule across the membrane for absorption.

Methods of Reducing Side Effects of an Agent by Converting it to an Orotate Derivative.

In a co-pending application, Ser. No. 11/063,943, filed Feb. 22, 2005 the inventor described the methods of increasing the oral bioavailability of pharmaceutical agents that are poorly absorbed from the gastrointestinal tract by converting them into orotate salts. In the present invention, the inventor describes a reduction in organ levels of drugs given as orotate derivatives, compared with the pharmaceutical form of the drug, thus reducing the potential for toxicity at the time of drug administration and in the long term after the primary cancer or disease is cured. Therefore, an especially useful formulation of the orotate derivative of the pharmaceutical agent can provide rapid onset and consistent action using a lower dose and reduce drug interactions and side-effects. All cited references are incorporated herein fully.

Orotic acid, a free pyrimidine is important in the synthesis of uridylate (UPP) a major pyrimidine nucleotide. Pyrimidines play a central role in cellular regulation and metabolism. They are substrates for DNA/RNA biosynthesis, regulators of the biosynthesis of some amino acids, and cofactors in the biosynthesis of phospholipids, glycolipids, sugars and polysaccharides. The classical de novo pyrimidine biosynthetic pathway ends with the sysnthesis of UMP. Biochemistry, Lubert Stryer, ed, W.H. Freeman & Co NY, $4^{th}$ ed, 739-762 (1995). It has also been reported that 5-Fluorouracil is toxic to the liver, as measured by incorporation in the acid soluble fraction, RNA and DNA in normal tissues in the liver of rats. Orotic acid administration decreased the incorporation into the liver and intestinal RNA, thus suggesting that it reduces 5-FU induced toxicity in the liver. El Hag I A et al, In vivo 1: 309-312 (1987). The present invention provides drug orotate derivatives that undergo dissolution to release the drug as a charged molecule and free orotic acid, which in turn reduces drug-induced liver, heart or other tissue toxicity.

The present invention provides methods and compositions to increase the effectiveness of a pharmaceutical agent by converting said pharmaceutical agent to an orotate derivative composition and, administering said orotate derivative to a subject in need thereof, said pharmaceutical agent selected from the group of consisting of acetanilide, actinomycin D adriamycin, aminoacridine, aminoimidazole, aminoquinoline, anilide, anthracycline antibiotic, antiestrogen, benzazepine, benzhydryl compound, benzodiazepine, benzofuran, cannabinoid, cephalosporine, cisplatin, colchicines, cyclic peptide, cyclophosphamide, daunorubicin, dibenzazepine, digitalis glycoside, dihydropyridine, doxorubicin, epiphodophyllotoxin, epirubicin, ergoline, ergot alkaloid, etoposide, 5-fluorouracil, idarubicin, ifosamide, imidazole, interleukin-2, interferon alpha isoquinoline, macrolide, melphalan, methotrexate, mitomycin-C, mitoxantrone, naphthalene, nitrogen mustard, opioid, oxazine, oxazole, paclitaxel, phenothiazine, phenylalkamine, phenylpiperidine, piperazine, piperidine, polycyclic aromatic hydrocarbon, pyridine, pyrimidine, pyrrolidine, pyrrolidinone, quinazoline, quinoline, quinine, rauwolfa alkaloid, retinoid, salicylate, steroid, stilbene, sulfone, sulfonylurea, tamoxifen, taxol, taxotere, THP-adriamycin, trastuzumab, triazole, tropane, vinblastine, vincristine or vinca alkaloid.

The invention provides methods and compositions to increase effectiveness of the orotate derivative of the pharmaceutical agent as measured by reduction in organ/tissue levels of the drug where the drug is known to cause toxicity or has the potential to induce toxicity in the long term because of tissue accumulation of the drug.

6. EXAMPLES

Example 1

Chemical Synthesis of Doxorubicin Orotate

Figure 1:
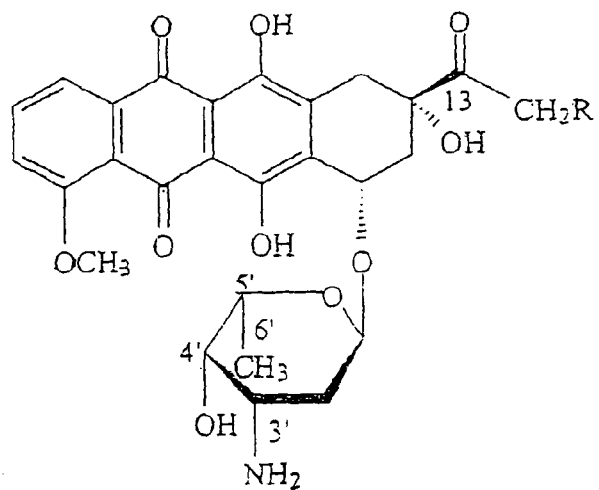
FIG. 1 illustrates the structures of daunorubicin and doxorubicin and their orotate derivatives.
Figure 2:
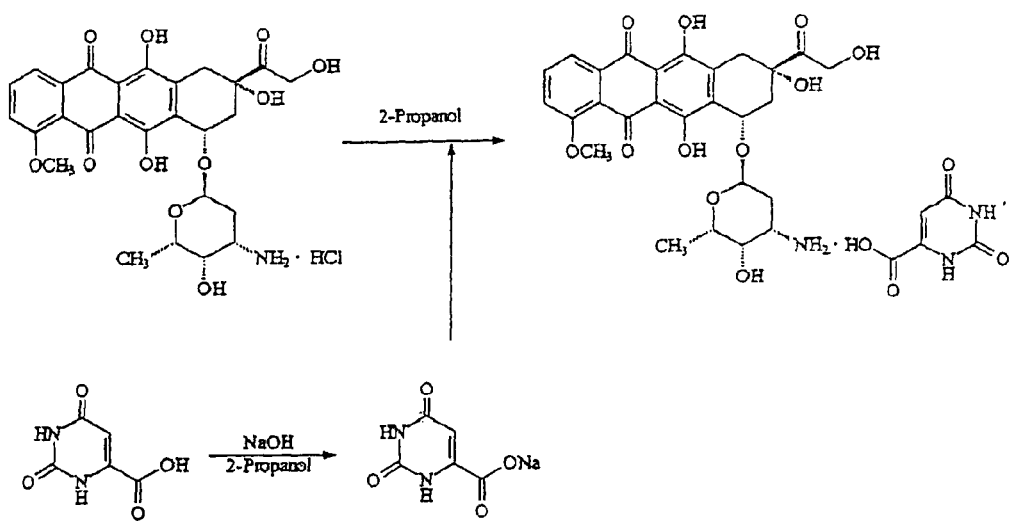
FIG. 2 illustrates the synthesis of doxorubicin orotate

FIG. 2 illustrates the synthesis of Doxorubicin Orotate. Orotic acid (1.0 g) was dissolved in 200 mL of water at 65° C. Potassium hydroxide (KOH) (1 eq) was added to the orotic acid and the mixture was stirred at 85° C. till a clear solution appeared. The solution was cooled, and the precipitate was collected by filtration to give a colorless solid (0.95 g), which was dried in vacuum for 24 hours. Mass Spectroscopy suggested that the structure was potassium orotate.

Potassium orotate (0.4 g) synthesized in the above step was dissolved in 150 mL of water at 65° C. The solution was de-aired in vacuum and protected with argon. Doxorubicin hydrochloride (1.0 g, 1 eq) was added and the resulting red solution was treated with excess amount of amberlite IR120H resin for 2 hours at the same temperature. After filtration the solution was frozen in dry ice, and lyophilized to give 1.35 g of doxorubicin orotate (J-1220-13-II) as a red solid. Mass Spectroscopy (FIG. 3) and Nuclear Magnetic Resonance (FIG. 4) indicate that the structure is doxorubicin orotate.

Example 2

Response of SC CAKI-1 Renal Tumor to Treatment with Doxorubicin HCl and Doxorubicin Orotate The purpose of the experiment was to evaluate the antitumor efficacy of doxorubicin hydrochloride (DOX) and its orotate derivative (DOX orotate) against subcutaneously (SC) implanted CAKI-1 human renal tumor xenografts in male athymic NCr-nu/nu mice. Hearts of the animals treated with DOX and DOX orotate at equivalent dose were analyzed and the concentration of DOX in the hearts of those animals was measured.

Drug formulation—0.8 mg/mL solution of DOX (Doxorubicin Hydrochloride USP29, Yick-Vic Chemical & Pharmaceuticals (HK) Ltd, Kowloon, Hong Kong, batch no M050705) was formulated fresh on each day of treatment in saline. The 0.8 mg/mL solution was diluted with saline to 0.53 and 0.35 mg/mL.

DOX orotate (lot no J1220-13-II) was synthesized from USP28, batch no. M050705, as described in Example 1. A 0.975 mg/mL solution of DOX orotate was formulated fresh on each day of treatment in saline. The 0.975 mg/mL solution was further diluted with saline to 0.65 and 0.43 mg/mL.

Both compounds and vehicle were administered to mice by animal's body weight on each day of treatment with the injection volume being 0.1 mL/10 g of body weight. Seven groups of 10 mice per group were injected intravenously once every four days for a total of 4 injections (q4d×4, Days 13, 17, 21 and 25) as follows: Group 1—saline, Groups 2, 3 and 4 with DOX at 8.0, 5.3, and 3.5 mg/kg/dose, respectively. Groups 5, 6, and 7 were treated with DOX orotate at dosages 9.75, 6.5 and 4.3 mg/kg/dose respectively (based on MW of DOX=580 and MW of DOX orotate=708).

Tumors were measured and volume determined using formula $L \times W^2/2 = mm^3$; and weight calculated assuming 1 $mm^3 = 1$ mg. The study was terminated 95 days after tumor implantation.

On day 26 (one day after the last injection) 5 animals from each of Groups 1, 2 and 5 were euthanized and the hearts were collected to measure doxorubicin levels.

Results:

Tumor weight—administration of DOX at dosages of 8.0, 5.3, and 3.5 mg/kg/dose (FIG. 5) and administration of DOX orotate at the equivalent dosages of 9.75, 6.5 and 4.3 mg/kg/dose, (FIG. 6) i.v., was very effective in the inhibition of the growth of CAKI-1 human renal tumor xenografts implanted s.c. in male NCr-nu/nu mice. There was no significant difference in tumor growth from administration of DOX orotate when compare with DOX indicating that i.v. administration of DOX orotate and DOX HCl had comparable antitumor effects (FIG. 7).

| | P Values | |
|---|---|---|
| Group Pairs | Time to 2 doubl.[a] | Weight on Day 26[b] |
| 1 vs. 2 | UE | <0.0001 |
| 1 vs. 3 | 0.000* | <0.0001 |
| 1 vs. 4 | 0.000 | <0.0001 |
| 1 vs. 5 | UE | <0.0001 |
| 1 vs. 6 | 0.000 | <0.0001 |
| 1 vs. 7 | 0.000 | <0.0001 |

Example 3

Determination of Doxorubicin in Mouse Heart

Concentration of doxorubicin was measured by HPLC Mass Spectrometry/Mass Spectrometry. It averaged 7,398 ng/g heart tissue for animals treated i.v. with DOX at the dosage of 8.0 mg/kg/dose (Group 2), and averaged 5,264 ng/g heart tissue for animals treated i.v. with DOX orotate at the dosage of 9.75 mg/kg/dose (Group 5). In other words, the tissue levels of doxorubicin in the heart tissue of animals treated with DOX orotate dropped by 28% when compared with tissue levels in heart tissue of DOX treated animals. Importantly, the heart tissue specimens were obtained one day after the last i.v. injection, therefore suggesting that even one day after the i.v. administration of the two different forms of DOX, there was a marked reduction in DOX levels with DOX orotate compared with DOX HCl. One skilled in the art would expect that the difference in heart DOX levels between the two groups will be even greater in the long term. This is because the effectiveness of DOX HCl is in part limited by the cumulative dose-related cardiotoxicity, which usually occurs late during a course of treatment or may present months or years after the completion of therapy. This suggests strongly that there may be drug residues left in the tissue after the therapy is completed. Therefore, there is a critical need to reduce and/or prevent the drug from accumulating immediately at termination of the therapy as well as subsequently in the short and long term in the noncancerous, normal or non-diseased tissue. The present invention provides the solution by providing the method and composition of doxorubicin as the DOX orotate derivative, which reduces the heart levels of DOX and thus make the heart safer from toxic effects of doxorubicin in the heart in the short and/or long term.

The present invention is not to be limited in scope by the embodiment disclosed in the example which is intended as an illustration of one aspect of the invention and any methods which are functionally equivalent are within the scope of the invention. Indeed, various modifications of the invention in addition to those shown and described herein will become apparent to those skilled in the art from the foregoing description. Such modifications are intended to fall within the scope of the appended claims.

Those skilled in the art will recognize, or be able to ascertain using no more than routine experimentation, any equivalents to the specific embodiments of the invention described herein. Such equivalents are intended to be encompassed by the claims.

What is claimed is:

1. A method of reducing levels of a pharmaceutical agent in noncancerous tissues, said method comprising the steps of a) converting said pharmaceutical agent to an orotate salt, and b) administering said orotate salt to a subject in need thereof, and measuring the levels of said pharmaceutical agent in noncancerous tissues, wherein said pharmaceutical agent is selected from the group consisting of daunorubicin and doxorubicin.

2. The method according to claim 1 wherein said composition of the orotate derivative produces a reduction in levels of the pharmaceutical agent by 25% relative to dosing of the pharmaceutical agent.

3. The method of claim 1, wherein said orotate salt is doxorubicin orotate.

4. A method of reducing levels of a pharmaceutical agent in noncancerous tissues comprising administering an orotate salt of doxorubicin to a subject, to increase clearance from noncancerous tissue levels of doxorubicin as measured by pharmacological studies at least 25% relative to dosing of the pharmaceutical agent.

5. A method of reducing adverse drug reaction of doxorubicin in a cancer patient, comprising converting said doxorubicin pharmaceutical agent to an orotate salt and administering said doxorubicin orotate salt to said patient.

* * * * *